United States Patent [19]

Rothen

[11] Patent Number: 4,982,688

[45] Date of Patent: Jan. 8, 1991

[54] APPARATUS FOR APPLYING GLUE TO ENDLESS THREADS

[75] Inventor: Josef Rothen, Solingen, Fed. Rep. of Germany

[73] Assignee: Macon Klebetechnik GmbH, Erkrath, Fed. Rep. of Germany

[21] Appl. No.: 292,175

[22] Filed: Dec. 30, 1988

[30] Foreign Application Priority Data

Dec. 31, 1987 [DE] Fed. Rep. of Germany ....... 3744587

[51] Int. Cl.$^5$ .................. B05C 3/12; B29C 47/02; B29C 47/12
[52] U.S. Cl. ................. 118/420; 425/113; 425/122; 425/466
[58] Field of Search .............. 239/456, 584; 264/174; 425/113, 122, 461, 466; 118/405, 420, 404

[56] References Cited

U.S. PATENT DOCUMENTS

| | | | |
|---|---|---|---|
| 2,608,950 | 9/1952 | Bradley | 118/125 |
| 4,208,837 | 11/1987 | Baxter et al. | 425/141 |
| 4,316,312 | 2/1982 | Vermeer et al. | 28/255 |
| 4,563,147 | 1/1986 | Langecker | 425/141 |

FOREIGN PATENT DOCUMENTS

| | | |
|---|---|---|
| 2240174 | 3/1975 | France . |
| 2226818 | 1/1976 | France . |
| 2274241 | 1/1976 | France . |
| 68293 | 6/1951 | Netherlands ........... 425/113 |

*Primary Examiner*—Willard Hoag
*Attorney, Agent, or Firm*—Foley & Lardner, Schwartz, Jeffery, Schwaab, Mack, Blumenthal & Evans

[57] ABSTRACT

Apparatus in which glue is applied to an endless thread by running the thread successively through the bore of a nozzle needle and a nozzle aperture and, when the nozzle needle is retracted from a valve seat, coating the thread with glue which has been forced out of a surrounding chamber. The thread, together with this coating, passes through the nozzle bore. As soon as the nozzle needle is advanced up against the valve seat in the nozzle element, the glue feed ceases and coating ends, so that the thread takes with it at most only very small quantities of glue remaining in the nozzle bore and an exact cutoff of the glue coating is obtained. When the glue is injected around the thread, that is, when the glue is brought together with the thread under a specific pressure exerted on all sides, it is possible to obtain a substantially uniform coating of the thread surface with glue which allows all improved bonding of the thread over its length to the sheet-like structure.

1 Claim, 1 Drawing Sheet

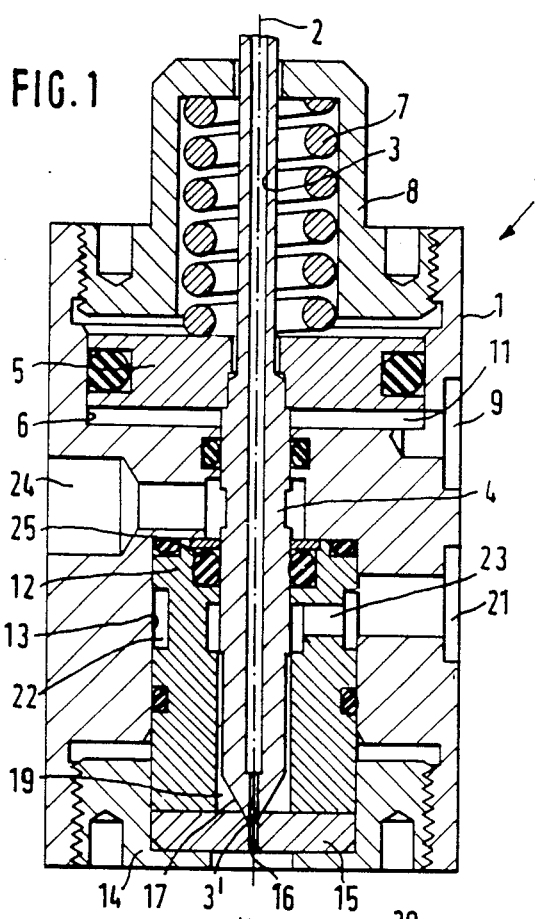
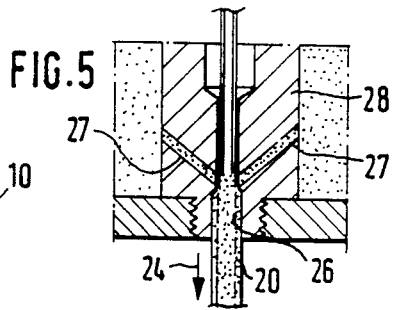
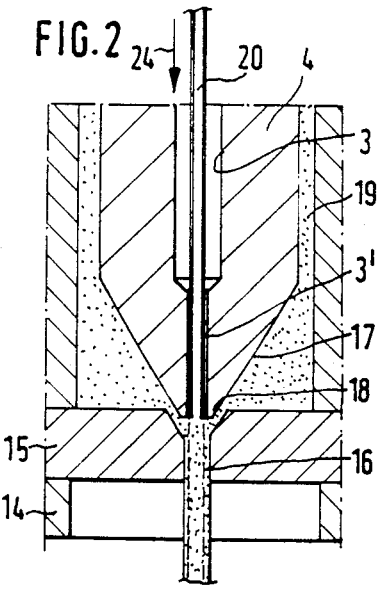
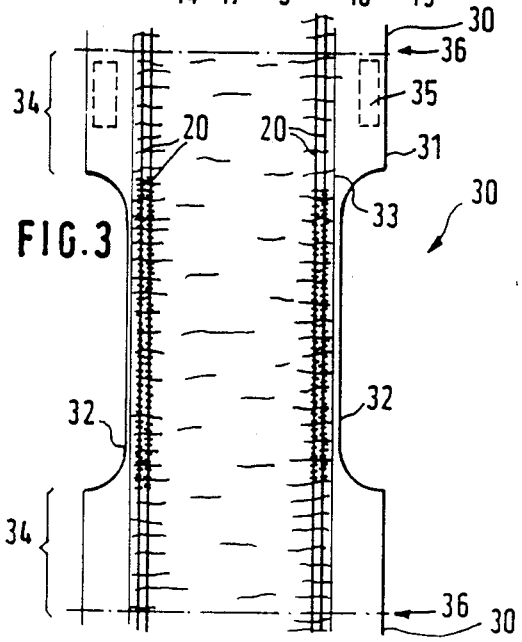
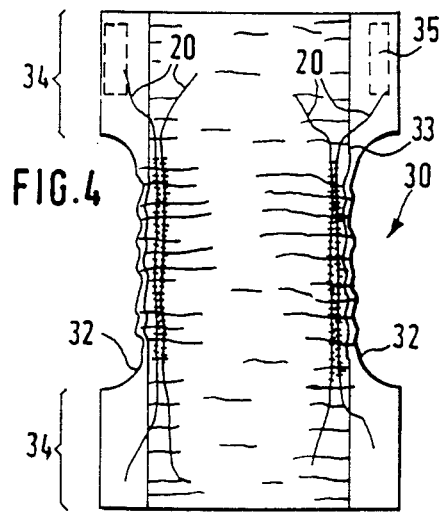

APPARATUS FOR APPLYING GLUE TO ENDLESS THREADS

BACKGROUND OF THE INVENTION

1. Field of the Invention

The invention relates to process and apparatuses for applying glue, and more particularly to a process and apparatus for controllably applying glue or another matrix material to continuous threads.

2. Discussion of the Related Art

In many commercial applications, it is desirable to effectively bond thread to another structure while using a minimal amount of adhesive. One such application involves the production of baby diapers. Diaper pants are composed of an essentially rectangular sheet-like structure which has a highly pliable impermeable film on the outside and an absorbent pad on the inside. Elongate leg cutouts are provided on the two longitudinal sides. Those regions of the diaper pants which project beyond the leg cutouts in the longitudinal direction are wrapped round the body at the front and rear and bonded together at the sides by means of an adhesive-film blank provided on the diaper pants.

The leg cutouts are intended to mold themselves to the leg gently, but sealingly, so that no fluid can escape at this location. To achieve this flexibility, the sheet-like structure is creped in the region of the leg cutouts and is thus elastically stretchable. The creping is obtained by means of one or more elastomeric threads which are arranged next to one another in the longitudinal direction within the edge of the leg cutout and which, in the stretched state, are bonded to the sheet-like structure over their entire length in the region of the leg cutouts. There should be no bonding in the regions projecting beyond the leg cutouts in the longitudinal direction, so that these regions are not creped and can be folded flat. Among other things, the elastomeric threads can be composed of rubber material or of textile material which, as a result of texturing, has acquired elastomeric properties in the longitudinal direction. An example of the latter is Lycra®, commercially available from E.I. Du Pont de Nemours and Company.

There are two known processes for bonding the elastomeric threads to the sheetlike structure of the diapers. In the first process, a glue track is formed on the sheet-like structure, and the elastomeric threads are pressed under prestress into this glue track. This process, however, is unsatisfactory, because the glue does not adhere well to the elastomeric threads. Furthermore, due to the glue track, a hardening of the sheet-like structure occurs in a zone where it is least desirable, that is, in the region of the edge of the leg cutouts.

In another process, the glue is applied to the threads by drawing these through a glue supply. As before, the adhesion of the threads to the sheetlike structure is unsatisfactory, because the threads do not readily accept the glue and frequently only individual, intermittent glue drops are caught on the thread.

SUMMARY OF THE INVENTION

The object of this invention is to provide a process and apparatus for applying glue to threads in such a way that a reliable bonding of the thread to a sheet-like structure is possible.

A further object of this invention is to provide a process and apparatus for applying glue guaranteeing an effective bond without using excess glue.

The foregoing objects and advantages are attained by running a thread successively through the bore of a nozzle needle and a nozzle aperture and, when the nozzle needle is retracted from a valve seat, coating the thread with glue which has been forced out of a surrounding chamber. The thread, together with this coating, passes through the nozzle bore. As soon as the nozzle needle is advanced up against the valve seat in the nozzle element, the glue feed ceases and coating ends, so that the thread takes with it at most only very small quantities of glue remaining in the nozzle bore and an exact cutoff of the glue coating is obtained.

When the glue is injected round the thread, that is, when the glue is brought together with the thread under a specific pressure exerted on all sides, it is possible to obtain a substantially uniform coating of the thread surface with glue which allows a good bonding of the thread over its length to the sheet-like structure.

It is especially advantageous that the glue can be applied to the already stretched thread easily and that, by interrupting the injection, the length of the glue-coated portions can be determined exactly, so that glue is applied only to the length portions of the thread which come to rest next to the leg cutouts.

The apparatus is equally suitable for elastomeric threads which are coated with glue in the stretched form and which are provided for particular uses, such as baby diapers, and for normal threads which have no appreciable stretching in the longitudinal direction and which are applied to paper bags, for example, for reinforcement.

At the front end, the bore of the nozzle needle will have its narrowest cross-section, through which the thread just fits without catching. The nozzle aperture has a somewhat larger diameter, so that there is room for the glue layer on the thread and the glue applied in the region of the valve seat is not scraped off again immediately. With the thread running at a predetermined speed, the difference in diameter meters the quantity of glue applied.

Since the nozzle element is designed as a nozzle plate, which in practice has a thickness in the range of 3 mm, for example, the length of the nozzle channel is small As a result of the engagement of the nozzle needle into a countersink of the nozzle plate, the glue is cut off in the region of the nozzle channel, so that after the closing of the glue valve formed by the nozzle needle, only a minimum quantity of glue remains in the front part of the nozzle aperture and is immediately taken up by the thread.

In the event of a failure of the pressure supplying means, the nozzle needle is moved into the closed position and no glue can escape from the nozzle aperture.

A crucial feature of the invention is that the glue is injected around the thread in a nozzle from all sides under a specific pressure, thereby necessarily forming a closed glue skin which is retained on the thread even when the latter comes out of the nozzle.

When the glue application is to be ended at a specific location on the thread, the valve arrangement is closed. When the valve arrangement is opened again, the built up pressure from the feedline may cause a pressure surge, so that a larger quantity of glue is applied until the pressure equalizes in the flow of the feed line. To prevent such an uneven application of glue, there can be a return channel with a valve arrangement, by means of which the conveyed glue can be returned to the pump when the glue outflow is closed. The pump, therefore, works continuously and is not affected by the closing of the glue outflow. Thus, the pressure in the feed line always remains at the same level, whether the glue is transferred to the thread at the glue outflow or is returned. The application of glue per unit of thread length is made uniform in this way.

Other advantages and objects of this invention will become apparent hereinafter in the specification and drawings which follow.

BRIEF DESCRIPTION OF THE DRAWINGS

FIG. 1 is a longitudinal section through the applicator head forming the apparatus according to the present invention;

FIG. 2 is an enlarged section of the nozzle aperture portion of FIG. 1;

FIG. 3 shows laid-flat baby diapers having elastomeric threads adhesively bonded thereto according to the present invention;

FIG. 4 shows the diaper pants of FIG. 3 after the threads have been severed;

FIG. 5 shows a modified embodiment of a nozzle according to the present invention.

DETAILED DESCRIPTION OF THE PREFERRED EMBODIMENTS

Referring to FIG. 1, the present invention contemplates an applicator head, designated generally by the reference numeral 10, comprising a block-like housing 1 having several recesses coaxial relative to an axis 2 and succeeding one another in the longitudinal direction. A nozzle needle 4 provided with a continuous longitudinal bore 3 and displaceable in the longitudinal direction is arranged in the recesses At a lower end, the outer face of the nozzle needle forms a conical surface 17 with an aperture angle in the range of about 60°. In the region of the cone, the nozzle needle 4 has an aperture part 3' of reduced diameter, through which a thread 20 to be coated with the glue just fits, without a strong pull being exerted on it. The rear part of the bore 3 has a somewhat larger diameter, so that the thread 20 can move through freely, as illustrated in FIG. 2.

In the middle portion of the apparatus, a disk-shaped piston 5 is screwed onto the nozzle needle 4 and is longitudinally moveable in a cylindrical chamber 6 of the housing 1. A helical compression spring 7 acts against the piston 5 from above, surrounds the upper part of the nozzle needle 4 and is accommodated in a cover 8 which is screwed into the top end of the housing 1. The nozzle needle 4 is therefore normally pressed downwards. Via an inlet 9, that part 11 of the cylindrical chamber 6 located under the piston 5 can be filled with a fluid pressure medium, for example compressed air, so that the piston 5 is moved upwards counter to the force of the spring 7 and thereby takes with it the nozzle needle 4.

In the lower region, the nozzle needle 4 is guided in a cylindrical insert 12 which is sealed-off in a cylindrical recess 13 of the housing and is retained therein by means of a cover 14 screwed into the lower end of the housing. Clamped between the cover 14 and the lower end face of the cylindrical insert 12 is a nozzle plate 15 having a nozzle channel 16 which is coaxial relative to the front aperture 3' of the bore 3 of the nozzle needle 4 and which has a slightly larger diameter than aperture 3'.

Under the effect of the spring 7, the nozzle needle 4 comes to rest with its conical front end 17 in a correspondingly conical countersink 18 of that end of the nozzle channel 16 facing the nozzle needle 4.

Formed around the front end of the nozzle needle 4 is a cylindrical chamber 19 of somewhat larger diameter, which can be supplied with glue via a feed channel 21, an annular channel 22 formed on the outer periphery of the cylindrical insert 12 and several radial channels 23 starting from the annular channel 22 and distributed over the periphery. The glue comes into the vicinity of the tip of the front conical surface 17 of the hollow needle 4. This conical surface 17 interacts in the manner of a valve with the countersink 18 forming a valve seat and, when no pressure prevails in the lower part 11 of the chamber 6 and the valve needle 4 is held up against the nozzle plate 15 by means of the spring 7, conical surface 17 shuts off the overflow of glue from the chamber 19 into the nozzle bore 16, as illustrated in FIG. 1.

However, when the nozzle needle 4 is retracted from the countersink 18 as a result of the introduction of compressed air into the part 11 of the chamber 6, glue overflows through the conical gap between the conical surface 17 and the countersink 18 into the nozzle channel 16 as shown in FIG. 2 and is taken up by thread 20 moving in the direction of the arrow 24'. The glue, therefore, forms an intrinsically coherent layer surrounding the thread 20 in a closed manner. So that there is room for the glue layer on the periphery of the thread 20, the diameter of the nozzle channel 16 is somewhat larger than the diameter of the thread 20 or of the aperture 3' of the bore 3.

If the pressure under the piston 5 is removed, the front end 17 is set again onto the countersink 18 and blocks the passage for the glue. The thread 20 continuing to run then no longer acquires any glue, and there is set a very exact cutoff of the coating.

So that no pressure surge occurs in the feed channel 21 when the valve created by surface 17 and countersink 18 is closed, and also so the pressure does not rise with the valve 17, 18 closed, there is a return channel (not shown) and a valve arrangement in which the glue guided through the feed channel 21 is automatically reversed into the return channel and to the pump when the valve 17, 18 is closed. The pump thus conveys continuously at a constant pressure, whether the valve 17, 18 is opened or closed. This ensures that, when the valve 17, 18 is opened again after a closed state, there is no increased initial pressure causing a greater application of glue, the glue application then gradually becoming normal again. This unevenness is prevented by the permanently closed glue circuit.

FIG. 5 illustrates an alternative embodiment of the nozzle. The thread 20 passes through a stationary needle 28, which corresponds to the nozzle needle 4, and at the front end of which is formed the nozzle 26. Glue is supplied via feed channels 27 distributed over the periphery and opening into the nozzle 26 from outside. The glue is then transferred onto the thread 20 advancing in the direction of the arrow 24'. Rising back into that part of the channel of the needle 28 having a larger diameter is prevented by the advancing movement of the thread 20.

The outlet 24 entering above the insert 12 serves for drawing off small quantities of glue which, for example, have overflowed upwards beyond the sealing means 25 during the lifting movement of the nozzle needle 4.

FIG. 3 illustrates a practical example of the use of the present invention in the production baby diapers. Baby diaper 30 comprises an essentially rectangular blank 31 and an impermeable film and having leg cutouts 32 located opposite one another on the two longitudinal sides. On the shorter sides, successive baby diaper pants 30 are connected to one another, for example, along a perforated edge, and thereby form a continuous web. A highly absorbent and also, under pressure, fluid-retaining pad 33 extending over the length of the diapers 30 and reaching near to the edge of the leg cutouts 32 is applied to the subsequent inner face.

When the diaper 30 is put on the child, the regions 34 projecting beyond the leg cutouts in the longitudinal direction are located respectively in front of and behind the body and are connected to one another at the sides by means of adhesive film blanks 35. The leg cutouts 32 then fully surround the baby's thigh and should rest against it as sealingly as possible. For this purpose, two elastomeric threads 20 which have been coated with glue in an applicator head 10 according to FIGS. 1 and 2 are glued on in the stretched state just within the edge of the leg cutout 32. Instead of two elastomeric threads 20 on each side, there can of course also be three or four. An applicator head 10 is provided for each thread 20. The various applicator heads 10 are arranged staggered in a suitable way, so that the threads can run exactly along the axis 2 and nevertheless can be applied very closely next to one another to the sheet-like structure forming the diaper 30, for example while the strip of diapers 30 is running round a drum.

The threads 20 are provided with glue only in the region of the longitudinal extension of the leg cutouts 32, but are free of glue in the projecting regions 34. The reason for this measure is clear from FIG. 4. After the threads 20 have been glued on, the individual diapers 30 are severed along the cutting lines 36. Since the threads 20 have been bonded to the baby diaper pants 30 in the stretched state, they contract in the region of the leg cutouts 32 as soon as severance has occurred along the lines 36, and thus cause a creping as shown in FIG. 4, due to the shortening of the material. This gives the material stretchability and is responsible for the sealed closure in the region of the leg cutouts 32.

However, the creping is to be restricted to the region of the leg cutouts 32. The regions 34 projecting in the axial direction are to remain planar. This is necessary both to ensure that the finished diapers 30 can be folded as flat as possible and also so they can be worn by the child. Those portions of the stretched threads 20 which are located in the regions 34 were not coated with glue and therefore snap back freely in the way indicated in FIG. 4, without a pull or a deformation having to be exerted on the material in the portions 34.

It should become obvious to those skilled in the art that the present invention is not limited to the preferred embodiments shown and described. For example, the process may be used to apply any injectable matrix material to any threadlike structure, such as in the pre-pregging of carbon fibers.

What is claimed is:

1. An apparatus for applying a matrix material to threadlike structures, comprising:
   a housing having a longitudinal axis;
   a nozzle needle displaceable in the housing parallel to said longitudinal axis;
   said nozzle needle having an axial bore through which a threadlike structure is guided;
   a chamber provided in the housing about a front end of the nozzle needle and being in fluid communication with a matrix material supplying means;
   a nozzle element arranged in the housing having a nozzle channel which is coaxial with said axial bore to receive a coated threadlike structure;
   said nozzle element having a valve seat reciprocating with said valve element of the nozzle needle;
   said nozzle needle having valve element disposed at a front end thereof;
   said valve element and valve seat forming an annular injecting channel therebetween;
   a drive means to controllably advance said nozzle needle toward said nozzle element until it abuts the valve seat to provide a seal; and
   a return channel having a valve arrangement means for returning the matrix material to the matrix supplying means when said valve element abuts said valve seat.

* * * * *